United States Patent
Shiau et al.

(10) Patent No.: US 8,729,112 B2
(45) Date of Patent: May 20, 2014

(54) ANTIMICROBIAL HALOALKYL HETEROCYCLE COMPOUNDS

(71) Applicant: NovaBay Pharmaceuticals, Inc., Emeryville, CA (US)

(72) Inventors: Timothy Shiau, Oakland, CA (US); Charles Francavilla, Fremont, CA (US); Eddy Low, Foster City, CA (US); Eric Douglas Turtle, Belmont, CA (US); Donogh John Roger O'Mahony, San Mateo, CA (US); Rakesh K. Jain, Danville, CA (US)

(73) Assignee: Novabay Pharmaceuticals, Inc., Emeryville, CA (US)

( * ) Notice: Subject to any disclaimer, the term of this patent is extended or adjusted under 35 U.S.C. 154(b) by 0 days.

(21) Appl. No.: 13/676,922

(22) Filed: Nov. 14, 2012

(65) Prior Publication Data

US 2014/0094495 A1 Apr. 3, 2014

Related U.S. Application Data

(60) Provisional application No. 61/559,414, filed on Nov. 14, 2011.

(51) Int. Cl.
*C07D 263/20* (2006.01)
*C07D 233/30* (2006.01)
*C07D 207/24* (2006.01)

(52) U.S. Cl.
USPC ........... 514/374; 514/392; 514/424; 548/229; 548/316.4; 548/543

(58) Field of Classification Search
CPC ... C07D 263/20; C07D 233/30; C07D 207/24
See application file for complete search history.

(56) References Cited

U.S. PATENT DOCUMENTS 4,049,818 A * 9/1977 Bodor et al. .................. 514/278

* cited by examiner

*Primary Examiner* — Kamal Saeed
(74) *Attorney, Agent, or Firm* — Sam L. Nguyen; Hamilton DeSanctis & Cha, LLP

(57) ABSTRACT

This application describes compounds useful as anti-microbial agents, including as antibacterial, disinfectant, antifungal, germicidal or antiviral agents.

12 Claims, No Drawings

ANTIMICROBIAL HALOALKYL HETEROCYCLE COMPOUNDS

RELATED APPLICATION

This application claims the benefit of U.S. Provisional Application No. 61/559,414 filed Nov. 14, 2011, which is incorporated herein by reference.

SUMMARY OF THE INVENTION

This application describes compounds useful as anti-microbial agents, including as antibacterial, disinfectant, antifungal, germicidal or antiviral agents.

One aspect of the current disclosure relates to compounds of Formula I

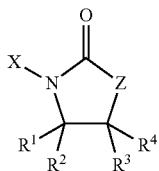

or a derivative thereof, wherein
X is Cl or Br;
Z is O, $NR^5$, or $CR^5R^6$; and
$R^1$, $R^2$, $R^3$, $R^4$, $R^5$ and $R^6$ are independently H, alkyl, or substituted alkyl,
with the proviso that at least one of $R^1$, $R^2$, $R^3$ and $R^4$ is a haloalkyl.

In some compounds of Formula I, X is Cl. In some compounds of Formula I, $R^3$ and $R^4$ are H. In some compounds of Formula I, the haloalkyl is a $C_1$-$C_6$ haloalkyl. In some compounds of Formula I, $R^1$ is a haloalkyl. In other compounds of Formula I, $R^1$ and $R^2$ are both, independently, haloalkyl. In some compounds of Formula I, $R^1$ is —$CH_2Cl$.

Another aspect of the current disclosure relates to compounds of Formula IA

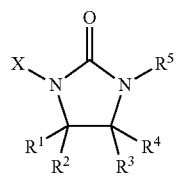

or a derivative thereof, wherein
X is Cl or Br; and
$R^1$, $R^2$, $R^3$, $R^4$ and $R^5$ are independently H, alkyl, or substituted alkyl,
with the proviso that at least one of $R^1$, $R^2$, $R^3$ and $R^4$ is a haloalkyl.

In some compounds of Formula IA, X is Cl. In some compounds of Formula IA, $R^1$ is a haloalkyl. In other compounds of Formula IB, $R^1$ and $R^2$ are both, independently, haloalkyl. In some compounds of Formula IB, $R^1$ is —$CH_2Cl$.

In some compounds of Formula IA, $R^3$ and $R^4$ are H. In other compounds of Formula IA, $R^3$ and $R^4$ are alkyl. In some compounds of Formula IA, $R^3$ and $R^4$ are methyl.

Another aspect of the current disclosure relates to compounds of Formula IB

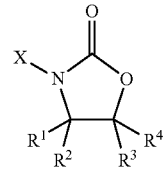

or a derivative thereof, wherein
X is Cl or Br; and
$R^1$, $R^2$, $R^3$, and $R^4$ are independently H, alkyl, or substituted alkyl,
with the proviso that at least one of $R^1$, $R^2$, $R^3$ and $R^4$ is a haloalkyl.

In some compounds of Formula IB, X is Cl. In some compounds of Formula IB, $R^1$ is a haloalkyl. In other compounds of Formula IB, $R^1$ and $R^2$ are both, independently, haloalkyl. In some compounds of Formula IB, $R^1$ is —$CH_2Cl$. In some compounds of Formula IB, $R^3$ and $R^4$ are H. In other compounds of Formula IB, $R^3$ and $R^4$ are alkyl. In some compounds of Formula IB, $R^3$ and $R^4$ are methyl.

Another aspect of the current disclosure relates to compounds of Formula IC

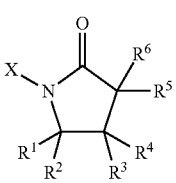

or a derivative thereof, wherein
X is Cl or Br; and
$R^1$, $R^2$, $R^3$, $R^4$, $R^5$ and $R^6$ are independently H, alkyl, or substituted alkyl,
with the proviso that at least one of $R^1$, $R^2$, $R^3$ and $R^4$ is a haloalkyl.

In some compounds of Formula IC, X is Cl. In some compounds of Formula IC, $R^1$ is a haloalkyl. In other compounds of Formula IC, $R^1$ and $R^2$ are both, independently, haloalkyl. In some compounds of Formula IC, $R^1$ is —$CH_2Cl$. In some compounds of Formula IC, $R^3$ and $R^4$ are H. In other compounds of Formula IC, $R^3$ and $R^4$ are alkyl. In some compounds of Formula IC, $R^3$ and $R^4$ are methyl. In some compounds of Formula IC, $R^5$ and $R^6$ are H. In other compounds of Formula IC, $R^5$ and $R^6$ are alkyl.

Specific examples of such compounds and other aspects of the current disclosure are described below.

Unless defined otherwise, all technical and scientific terms used herein have the same meaning as commonly understood by one of ordinary skill in the art. It must be noted that as used herein and in the appended claims, the singular forms "a", "and", and "the" include plural referents unless the context clearly dictates otherwise. Thus, e.g., reference to "the compound" includes a plurality of such compounds and reference to "the assay" includes reference to one or more assays and equivalents thereof known to those skilled in the art, and so forth.

Certain commonly used alternative chemical names may or may not be used. For example, a divalent group such as a divalent "alkyl" group, a divalent "aryl" group, etc., may also be referred to as an "alkylene" group or an "alkylenyl" group, an "arylene" group or an "arylenyl" group, respectively.

As utilized in accordance with the present disclosure, the following terms, unless otherwise indicated, shall be understood to have the following meanings:

"Alkyl" refers to any aliphatic hydrocarbon group, i.e. any linear, branched or cyclic nonaromatic hydrocarbon group or an isomer or combination thereof. As used herein, the term "alkyl" includes terms used in the art to describe saturated and unsaturated aliphatic hydrocarbon groups with one or more points of attachment, including alkenyl (an aliphatic group containing at least one carbon-carbon double bond), alkylene (a divalent aliphatic group), alkynyl (an aliphatic group containing at least one carbon-carbon triple bond), cycloalkyl (a cyclic aliphatic group), alkylcycloalkyl (a linear or branched aliphatic group attached to a cyclic aliphatic group), and the like. Alkyl groups include, but are not limited to, methyl; ethyl; propyls such as propan-1-yl, propan-2-yl (iso-propyl), cyclopropan-1-yl, etc.; butyls such as butan-1-yl, butan-2-yl (sec-butyl), 2-methyl-propan-1-yl (iso-butyl), 2-methyl-propan-2-yl (t-butyl), cyclobutan-1-yl; pentyls; hexyls; octyls; dodecyls; octadecyls; cyclopentyl, cyclohexyl, methylcyclohexyl, and the like. An alkyl group comprises from 1 to about 22 carbon atoms, e.g., from 1 to 22 carbon atoms (i.e., $C_{1-22}$ alkyl), e.g. from 1 to 12 carbon atoms, or, e.g., from 1 to 6 carbon atoms (i.e., $C_{1-6}$ alkyl).

"Acyl" refers to a group —C(=O)R, where R is hydrogen, alkyl, cycloalkyl, cycloheteroalkyl, aryl, arylalkyl, heteroalkyl, heteroaryl or heteroarylalkyl as defined herein, each of which may be optionally substituted, as defined herein. Representative examples include, but are not limited to formyl, acetyl, cylcohexylcarbonyl, cyclohexylmethylcarbonyl, benzoyl, benzyloxycarbonyl and the like.

"Acylamino" (or alternatively "acylamido") refers to a group $R^1R^2NC(=O)$—, —$NC(=O)R^1R^2$, where $R^1$ and $R^2$ are each independently hydrogen, alkyl, cycloalkyl, cycloheteroalkyl, aryl, arylalkyl, heteroalkyl, heteroaryl or heteroarylalkyl, as defined herein, each of which may be optionally substituted, as defined herein. Representative examples include, but are not limited to, formylamino, acetylamino (i.e., acetamido), cyclohexylcarbonylamino, cyclohexylmethyl-carbonylamino, benzoylamino (i.e., benzamido), benzylaxycarbonylamino and the like.

"Alkoxy" refers to a group —OR where R represents an alkyl or cycloalkyl group as defined herein, each of which may be optionally substituted, as defined herein. Representative examples include, but are not limited to, methoxy, ethoxy, propoxy, butoxy, cyclohexyloxy and the like.

"Aryl" refers to a group with one or more aromatic rings. It may be a single aromatic ring or multiple aromatic rings which are fused together, linked covalently, or linked via one or more such as a methylene or ethylene moiety. Aryls include, but are not limited to, those groups derived from acenaphthylene, anthracene, azulene, benzene, biphenyl, chrysene, cyclopentadienyl anion, diphenylmethyl, fluoranthene, fluorene, indane, indene, naphthalene, perylene, phenalene, phenanthrene, pyrene, triphenylene, and the like. An aryl group comprises from 5 to about 20 carbon atoms, e.g., from 6 to 20 carbon atoms, e.g. from 5 to 10 carbon atoms.

"Arylalkyl" (also "aralkyl") refers to an aryl group attached to an alkyl group. Arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like.

Where specific alkyl moieties are intended, the nomenclature arylalkanyl, arylalkenyl and/or arylalkynyl may be used. An arylalkyl group comprises from 7 to about 42 carbon atoms, e.g. the alkyl group can comprise from 1 to about 22 carbon atoms and the aryl group can comprise from 6 to about 20 carbon atoms.

"Compounds" as used herein refers to any of the compounds encompassed by Formula I (which include compounds of Formulae IA, IB and IC) as disclosed herein. The compounds may be neutral, charged (e.g. cationic or anionic), or in a salt form. The compounds may be identified by structure and/or by name. If the chemical structure and chemical name conflict, the chemical structure will be determinative of the identity of the compound. The compounds may contain one or more chiral centers and/or double bonds and therefore, may exist as stereoisomers, such as double-bond isomers (i.e., geometric isomers), enantiomers or diastereomers. Accordingly, when stereochemistry at chiral centers is not specified, the chemical structures depicted herein encompass all possible configurations at those chiral centers including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated compounds. The compounds also include isotopically labeled compounds where one or more atoms have an atomic mass different from the atomic mass conventionally found in nature. Examples of isotopes that may be incorporated into the compounds include, but are not limited to, $^2H$, $^3H$, $^{13}C$, $^{14}C$, $^{15}N$, $^{17}O$, $^{18}O$, $^{18}F$, $^{31}P$, $^{32}P$, $^{35}S$ and $^{36}Cl$. Compounds may exist in unsolvated forms as well as solvated forms, including hydrated forms. In general, the neutral, charged, protonated, salt, hydrated, solvated and N-oxide forms are within the scope of the present disclosure.

"Derivative" refers to salts, esters, amides, prodrugs, and tautomers of compounds described herein, including salts of those esters, amides, prodrugs, and tautomers. Derivatives include pharmaceutically acceptable derivatives, including pharmaceutically acceptable salts, esters and prodrugs.

"Effective amount" refers to the amount of a compound that, when administered to a subject, surface or area for treating or preventing a microbial infection or contamination, is sufficient to effect such treatment or prevention. The "effective amount" will vary depending on the compound, the severity of the condition causing the microbial infection and the age, weight, etc., of the subject to be treated.

"Electron-withdrawing" refers to one of more atoms or functional groups which are electronegative either through a resonance effect or an inductive effect. Examples of such atoms and functional groups include, but are not limited to —$CO_2R^0$, —CO—, —$NO_2$, —$SO_3R^0$, —$PO_3R^0R^{00}$, cyano, halogen (F, Cl, Br, I), and haloalkyl (e.g. —$CF_3$), where $R^0$ and $R^{00}$ are independently H, alkyl, aryl, cycloalkyl, heteroalkyl, heteroaryl or cycloheteroalkyl group, as defined herein, each of which may be optionally and independently substituted.

"Group" when used in a chemical context, refers to a chemical group, moiety or radical.

"Halide" refers to a halogen bearing a negative charge, including fluoride, chloride, bromide, and iodide.

"Halo" refers to a halogen, including fluoro, chloro, bromo, and iodo.

"Heteroalkyl" refers to an alkyl group in which one or more of the carbon atoms (and any associated hydrogen atoms) are each independently replaced with the same or different a heteroatomic group. Heteroatoms include, but are not limited to, N, P, O, S, etc. Heteroatomic groups include, but are not limited to, —NR$^O$—, —O—, —S—, —PH—, —P(O)$_2$—, —S(O)—, —S(O)$_2$—, and the like, where R$^O$ is defined above. The term "heteroalkyl" includes heterocycloalkyl (a cyclic heteroalkyl group), alkyl-heterocycloalkyl (a linear or branched aliphatic group attached to a cyclic heteroalkyl group), and the like. Heteroalkyl groups include, but are not limited to, —OCH$_3$, —CH$_2$OCH$_3$, —SCH$_3$, —CH$_2$SCH$_3$, —NR$^O$CH$_3$, —CH$_2$NR$^{OO}$CH$_3$, and the like, where R$^O$ and R$^{OO}$ are defined above. A heteroalkyl group comprises from 1 to about 22 carbon and hetero atoms, e.g., from 1 to 22 carbon and heteroatoms, e.g. from 1 to 12 carbon and hetero atoms, e.g., from 1 to 6 carbon and hetero atoms.

"Heteroaryl" refers to an aryl group in which one or more of the carbon atoms (and any associated hydrogen atoms) are each independently replaced with the same or different heteroatomic groups, as defined above. Heteroaryl groups include, but are not limited to, groups derived from acridine, carbazole, carboline, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. A heteroaryl group comprises from 5 to about 20 atoms, e.g., from 5 to 20 atoms, e.g. from 5 to 10 atoms.

"Heterocycloalkyl" is a subset of "heteroalkyl" and refers to a saturated or unsaturated cycloalkyl group in which one or more carbon atoms (and any associated hydrogen atoms) are independently replaced with the same or different heteroatom. Heteroatoms include, but are not limited to, N, P, O, S, etc. A heterocycloalkyl group may also contain a charged heteroatom or group, e.g., a quaternized ammonium group such as —N$^+$(R)$_2$— wherein R is alkyl, e.g., methyl, ethyl, etc. Heterocycloalkyl groups include, but are not limited to, groups derived from epoxides, imidazolidine, morpholine, piperazine, piperidine, pyrazolidine, piperidine, pyrrolidine, quinuclidine, N-bromopyrrolidine, N-bromopiperidine, N-chloropyrrolidine, N-chloropiperidine, an N,N-dialkylpyrrolidinium, such as N,N-dimethylpyrrolidinium, a N,N-dialkylpiperidinium such as N,N-dimethylpiperidium, and the like. The heterocycloalkyl group comprises from 3 to about 10 carbon and hetero atoms in the ring.

"Optionally" means that the subsequently defined event or circumstance may or may not occur, and that the description includes instances where the event or circumstance occurs and instances in which it does not. For example, an "optionally substituted aryl or heteroaryl" refers to an aryl or heteroaryl group, either of which may be substituted (as defined below) or not.

"Pharmaceutically acceptable" refers to that which is useful in preparing a pharmaceutical composition that is generally safe, non-toxic, and neither biologically nor otherwise undesirable, and includes that which is acceptable for veterinary or human pharmaceutical use.

"Pharmaceutically acceptable salt" refers to a salt of a compound that is pharmaceutically acceptable and that possesses (or can be converted to a form that possesses) the desired pharmacological activity of the parent compound. Such salts include acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic acid, camphorsulfonic acid, citric acid, ethanesulfonic acid, fumaric acid, glucoheptonic acid, gluconic acid, lactic acid, maleic acid, malonic acid, mandelic acid, methanesulfonic acid, 2-napththalenesulfonic acid, oleic acid, palmitic acid, propionic acid, stearic acid, succinic acid, tartaric acid, p-toluenesulfonic acid, trimethylacetic acid, and the like, and salts formed when an acidic proton present in the parent compound is replaced by either a metal ion, e.g., an alkali metal ion, an alkaline earth ion, or an aluminum ion; or coordinates with an organic base such as diethanolamine, triethanolamine, N-methylglucamine and the like. Also included in this definition are ammonium and substituted or quaternized ammonium salts. Representative non-limiting lists of pharmaceutically acceptable salts can be found in S. M. Berge et al., *J. Pharma Sci.*, 66(1), 1-19 (1977), and *Remington: The Science and Practice of Pharmacy*, R. Hendrickson, ed., 21st edition, Lippincott, Williams & Wilkins, Philadelphia, Pa., (2005), at p. 732, Table 38-5, both of which are hereby incorporated by reference herein.

"Pharmaceutically acceptable carrier" refers to a pharmaceutically acceptable diluent, adjuvant, excipient or vehicle and the like with which a compound is combined and/or administered.

"Pharmaceutical composition" as used herein comprises one or more compounds of Formula I and a pharmaceutically acceptable carrier.

"Prevent", "preventing" and "prevention" of a microbial infection refer to reducing the risk of a subject from developing a microbial infection, or reducing the frequency or severity of a microbial infection in a subject.

"Prodrug" and "prodrugs" refer to compounds that are rapidly transformed in vivo to yield a compound of the Formulae describe herein, for example by hydrolysis (chemical or enzymatic). By way of example but not limitation, one type of prodrug is esters, for example esters derived from pharmaceutically acceptable aliphatic carboxylic acids such as formates, acetates, propionates, butyrates, acrylates, ethylsuccinates, and the like. Further examples of prodrugs can be found in J. Rautio et al. *Prodrugs: design and clinical applications*, Nat. Rev. Drug Discov., 7, 255-270 (2008).

"Protecting group" refers to a group of atoms that when attached to a reactive functional group in a molecule masks, reduces or prevents reactivity of the functional group. Examples of protecting groups can be found in P. G. M. Wuts and T. W. Greene, *Greene's Protective Groups in Organic Synthesis* (4th Ed.), Wiley-Interscience, (2006), and Harrison et al., *Compendium of Synthetic Organic Methods*, Vols. 1-8 (John Wiley and Sons, 1971-1996). For example, representative amino protecting groups include, but are not limited to, formyl, acetyl, trifluoroacetyl, benzyl, benzyloxycarbonyl ("CBZ", "Cbz"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Salt" refers to a cation coupled with an anion, either in solution or as a solid. Salts include pharmaceutically acceptable salts as well as solvent addition forms (solvates) of the same salt.

"Subject" refers to humans and wild or domestic animals including, without limitation, horses, cattle, swine, birds, dogs, cats, monotremes, and the like.

"Sulfate" refers to the group $SO_4^{-2}$.

"Substituted" as in, for example, "substituted alkyl," refers to a group, for example an alkyl group, wherein one or more hydrogens (e.g., from 1 to 5, e.g., from 1 to 3) have been independently replaced with one or more substituents including, but not limited to, acylamino, alkoxy, alkyl, amino, amidino, aryl, carboxyl, carbamoyl, cyano, cycloalkyl, guanidino, halo, heteroalkyl, heteroaryl, heterocycloalkyl, hydroxyl, imidino, imino, nitro, oxamidino, oxo, methoxamidino, sulfonamido, thio, thioamido, an electron-withdrawing group, or a combination thereof.

"Treat", "treating" and "treatment" of a microbial infection or contamination refer to reducing the frequency or severity of symptoms of a microbial infection (including eliminating them), or avoiding or reducing the chances of the occurrence of a microbial infection, or killing or inhibiting the growth of bacteria, fungus or virus or associated biofilm.

The following abbreviations may also be used: APCI: atmospheric pressure chemical ionization; $Boc_2O$: di-tert-butyl dicarbonate; Cmpd: compound; DCM: dichloromethane, also known as methylene chloride; DIEA: diisopropylethylamine; DMF: N,N-dimethylformamide; EDT: ethanedithiol; ESI: electrospray ionization; EtOAc: ethyl acetate; EtOH: ethanol; h: hour; HPLC: high pressure liquid chromatography; LCMS: high pressure liquid chromatography with mass spectrometer detector; MeOH: methanol; m/z: mass to charge ratio; NMR: nuclear magnetic resonance; pos: positive; PTFE: polytetrafluoroethylene; RT or rt: room temperature; sat.: saturated; TFA: trifluoroacetic acid; TLC: thin layer chromatography. Other abbreviations commonly used in the art may also be used.

The present application includes the compounds in Table 1, hereby identified by name, structure, and compound number. These and other compounds may be named or depicted with or without a particular counter ion (e.g., chloride or Cl⁻), if appropriate. It will nevertheless be understood that in those cases, the associated cation and any other salt form (e.g., the corresponding bromide, carbonate, hydroxide, etc.), as well as the particular salt named or depicted, may also be contemplated and are within the scope of this disclosure.

TABLE 1

| Name (Compound Number) | Structure |
|---|---|
| 3-Chloro-4-(chloromethyl)-4-methyloxazolidin-2-one (36-1) | |
| 3-Chloro-4-(chloromethyl)-1,4-dimethylimidazolidin-2-one (36-2) | 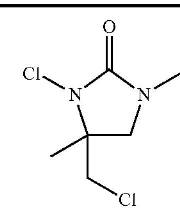 |
| 1-Chloro-5-(hydroxymethyl)-5-methylpyrrolidin-2-one (36-3) | 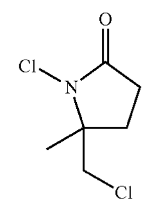 |
| 3-bromo-4-(chloromethyl)-4-methyloxazolidin-2-one (36-4) | 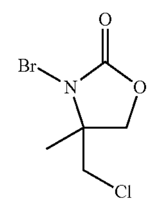 |
| 4-(Bromomethyl)-3-chloro-4-methyloxazolidin-2-one (36-5) | 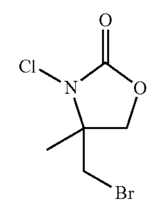 |
| 3-Chloro-4,4-bis(chloromethyl)oxazolidin-2-one (36-6) | |

Salts of the compounds of the present application may be prepared by reacting the free acid or base moieties of these compounds, where present, with a stoichiometric or greater amount of the appropriate base or acid in water or in an organic solvent, or in a mixture of the two; generally, e.g., non-aqueous media like ether, ethyl acetate, ethanol, isopropanol. The salts of the present application may also be prepared by ion exchange.

Compounds of Formula I (which include compounds of Formulae IA, IB and IC) may be formulated as solids, liquids, gels, aerosols, and other forms. For example, solid formulations may consist primarily of a compound of Formula I as a salt. Compositions comprising one or more compounds of Formula I and one or more other substances (e.g. excipients) may be formed, and may take the form of aerosols, creams, emulsions, gels, lotions, ointments, pastes, powders, solutions, suspensions, and other forms suitable for their intended use or application.

Compositions or formulations may include a pharmaceutically acceptable carrier, as defined above. By way of example, the compositions of the present application may include the following pharmaceutically acceptable carriers:

sodium chloride to attain isotonicity, buffers, stabilizers, solvents, flavoring agents (in case of oral or nasopharyngeal administration or the food industry), preserving agents, diluents, extenders and other auxiliary substances or excipients. Examples of pharmaceutically acceptable carriers and excipients that may be used are described in *Remington: The Science and Practice of Pharmacy*, R. Hendrickson, ed., 21st edition, Lippincott, Williams & Wilkins, Philadelphia, Pa., (2005) at pages 317-318, which are hereby incorporated by reference in their entireties. In general, water, saline, oils, alcohols (e.g. 2-propanol, 1-butanol, etc.), polyols (e.g. 1,2-propanediol, 2,3-butanediol, etc.), and glycols (e.g. propylene glycol, polyethylene glycols, etc.) may be suitable carriers for solutions. In one aspect solutions contain the active ingredient in a water soluble or aqueous medium soluble form, e.g. as a salt, together with suitable stabilizing agents, and if necessary, buffer substances.

For example, compounds of Formula I may be formulated with cyclodextrin or cyclodextrin derivatives, including cyclodextrin sulfobutyl ether (Capisol®, Cydex Pharmaceuticals, Inc., Overland Park, Kans., USA). These and other carriers may be used to improve or otherwise modulate the solubility, penetration, uptake, and other properties of compositions comprising the compounds described herein.

Aerosols can range from colloidal dispersions to formulations designed for pressurized delivery. Modes of operation include liquefied-gas systems, compressed-gas systems, and barrier-type systems.

Creams are viscous liquids or semisolid emulsions, either oil-in-water or water-in-oil. Cream bases are water-washable, and contain an oil phase, an emulsifier and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant.

Emulsions are two-phase systems prepared by combining two immiscible liquids, in which small globules of one liquid are dispersed uniformly throughout the other liquid. Emulsions may be designated as oil-in-water or water-in-oil type emulsions. Certain emulsions may not be classified as such because they are described by another category, such as a lotion, cream, and the like.

Gels are semisolid, suspension-type systems. Single-phase gels contain organic macromolecules distributed substantially uniformly throughout the carrier liquid, which is typically aqueous, but also, e.g., contain an alcohol such as ethanol or isopropanol and, optionally, an oil. Exemplary gelling agents include crosslinked acrylic acid polymers such as the "carbomer" family of polymers, e.g., carboxypolyalkylenes that may be obtained commercially under the Carbopol® trademark. Also useful are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Lotions are preparations generally applied to the skin surface so as to avoid high friction, and are typically liquid or semiliquid preparations in which solid particles, including the active agent, are present in a water or alcohol base. Lotions are usually suspensions of solids, and, e.g., comprise a liquid oily emulsion of the oil-in-water type. Lotions can be used to large body areas, because of the ease of applying a generally fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethyl-cellulose, or the like.

Ointments are semi-solid preparations that are typically based on petrolatum or other petroleum derivatives. The specific ointment base to be used is one that will provide for optimum active ingredient delivery, and other desired characteristics, e.g., emolliency. As with other carriers or vehicles, an ointment base should be inert, stable, nonirritating and nonsensitizing. Ointment bases may be grouped in four classes: oleaginous bases, emulsifiable bases, emulsion bases and water-soluble bases. Oleaginous ointment bases include, e.g., vegetable oils, fats obtained from animals, and semisolid hydrocarbons obtained from petroleum. Emulsifiable ointment bases, also known as absorbent ointment bases, contain little or no water and include, e.g., hydroxystearin sulfate, anhydrous lanolin and hydrophilic petrolatum. Emulsion ointment bases are either water-in-oil (W/O) emulsions or oil-in-water (O/W) emulsions, and include, e.g., cetyl alcohol, glyceryl monostearate, lanolin and stearic acid. For example, water-soluble ointment bases are prepared from polyethylene glycols of varying molecular weight.

Pastes are semisolid dosage forms in which the active agent is suspended in a suitable base. Depending on the nature of the base, pastes are divided between fatty pastes or those made from single-phase aqueous gels. The base in a fatty paste is generally petrolatum or hydrophilic petrolatum or the like. The pastes made from single-phase aqueous gels generally incorporate carboxymethylcellulose or the like as a base.

Suspensions may be defined as a coarse dispersion containing finely divided insoluble material suspended in a liquid medium.

Formulations may also be prepared with liposomes, micelles, and microspheres.

Various additives may also be included in formulations, e.g. to solubilize the active ingredients. Other optional additives include opacifiers, antioxidants, fragrances, colorants, gelling agents, thickening agents, stabilizers, surfactants and the like.

These and other compositions or formulations suitable for carrying and delivering compounds of Formula I are described in Chapters 22, 39, 43, 45, 50 and 55 of *Remington*, above, which are hereby incorporated by reference in their entireties.

The concentration of compounds of Formula I in compositions, formulations and dosage forms may be up to the saturation concentration of those compounds (or salts), e.g., up to about 1 M (molar), up to about 500 mM (millimolar), or up to about 150 mM. For example, compositions of the present application can comprise a concentration of a compound of Formula I (or its salt) ranging from about 0.001 mM to about 1 M, from about 0.01 mM to about 500 mM, from about 0.05 mM to about 150 mM, from about 0.1 mM to about 10 mM, and about 0.5 mM to about 2 mM.

In a further aspect, compositions of the present application comprise isotonic or physiologically balanced solutions of compounds of Formula I or their salts.

The compounds of Formula I (including Formula IA, IB, and IC), or their salts, are useful in methods of preventing or treating microbial (e.g. bacterial, viral, fungal, or protazoal)

infection or contamination. Compounds described herein may also be administered to prevent or treat a disease, disorder, ailment, or other pathology caused by bacteria or associated biofilm, fungus, virus, or protozoa. The compounds or salts described herein may also be used for the preparation of a medicine for the prevention or treatment of microbial infection, contamination or activity in a subject. Such methods comprise administering or applying an effective amount of the compound or salt thereof in or near the area of interest, e.g. in or near a tissue or organ, to a surface of a medical device, within a storage container, and so on.

Compositions described herein have antimicrobial activity against a broad range of microorganisms. Table 2 (see Example 7, below) shows activity of selected compounds against *Escherichia coli, Staphylococcus aureus*, and *Candida albicans*, representative microbial species. These compounds may be effective against other organisms including *Haemophilus influenzae, Enterococcus faecium, Enterococcus faecalis, Listeria monocytogenes*, methicillin-resistant *S. aureus* (MRSA), *Staphylococcus epidermidis, Streptococcus pneumoniae, Pseudomonas aeruginosa, Proteus mirabilis, Klebsiella pneumoniae, Lactobacillus* spp., *Acinetobacter junii*, yeast, (e.g. *Candida albicans*), vancomycin-resistant *Enterococcus* spp., molds, *Acanthamoeba* and other species of amoeba, and spores, including spores of anthrax and cysts of *Acanthamoeba* spp.

Compositions of the present application are useful in a wide range or applications in which antimicrobial properties are desirable. Such applications include, without limitation, treatment or reduction of pathogens on or in the skin, nails, hair or mucous membranes, wounds, surgical sites, and so forth. Applications and areas of interest include wounds, burns, ulcers, inflammation or lesions of the skin, the eyes, ears, nasal passages, sinus, bronchopulmonary system, vagina, rectum and other mucous membranes or related tissues.

While N-halogenated compounds of Formula I (including Formulas IA, IB and IC) may have inherent antimicrobial activity, the corresponding N-protonated (i.e. non-halogenated) analogs may also have antimicrobial activity, or may be activated to an antimicrobial (or increased antimicrobial) state by a source of halogen. For example, it is well known that hypochlorite and/or hypochlorous acid is generated by neutrophils, eosinophils, mononuclear phagocytes, and B lymphocytes [see, e.g., L. Wang et al., *J. Burns Wounds*, 6, 65-79 (2007) and M. Nagl et al., *Antimicrob. Agents Chemother.* 44(9) 2507-13 (2000)]. Certain organic chloramines, including N-chlorotaurine, have been detected in the supernatants of stimulated granulocytes, and are thought to prolong the oxidative capacity of these cells during oxidative burst and to protect cells from damage by HOCl/OCl$^-$. In a similar fashion to taurine, N-protonated compounds of Formula I in or near these cells may be chlorinated during oxidative burst, and may serve a similar microbicidal and/or protective effect. Thus, compounds of Formula I may be used in methods to generate antimicrobial activity in situ, to prolong or otherwise modulate the oxidative capacity of cells during oxidative burst, or to decrease associated cyclotoxicity.

The compounds described herein may also be useful in a method to decontaminate, disinfect, or clean surfaces of materials, devices, or equipment, the method comprising contacting the material, device, or equipment with a solution comprising a compound or salt thereof. For example, a solution comprising a compound of Formula I can be applied by spray or an applicator such as a cotton ball or cloth to the medical device, or the medical device can be immersed in said solution. Applications include the elimination or reduction of pathogens (e.g. bacteria, virus, fungus, microbe, etc.) on or in medical (including surgical, dental, optical, and other) devices, equipment and instruments, (e.g. breathing tubes, catheters, contact lenses, dental implants and equipment, equipment used for organ preservation, hearing aids, prostheses, stents, etc.), devices, food (e.g., meats, fish, fruits, vegetables, nuts, etc.) and food contact surfaces (e.g. cutting tools, cutting surfaces, storage rooms or containers, etc.) including the elimination or reduction of bacterial biofilms, and agricultural uses including protection of seed stocks.

By way of example, compounds and compositions of the present application may be used for the eradication of bacteria (including bacteria in a biofilm), such as, but not limited to, bacterial and biofilms in or on medical devices, e.g. in the lumen of a catheter (e.g. urinary, central venous, hemodialysis catheters and the like), stent, breathing tube, etc. Such methods may include the destruction of the corresponding biofilm matrix to clear the bacterial load from the medical device, such as improving or maintaining patency in the lumen of a catheter, stent, or breathing tube. Biofilms are a group of microorganisms attached to a substrate and are often associated with the excretion of extracelullar polymeric substance [R. M. Donlan et al., *Clin. Microbiol. Rev.*, 4, 167-193 (2002)]. The demonstrated resistance of biofilms to antimicrobials has caused problems in human health and has had a significant impact on the success of medical implants, e.g., catheters [J. W. Costerton et al., *Science,* 284(5418), 1318-22 (1999)]. Once catheters are colonized, biofims will develop on the outer and inner surfaces and cause infections. Reduction of the bacterial load by prevention of the formation of biofilm [J. F. Williams and S. D. Worley, *J. Endourology,* 14(5), 395-400 (2000); K. Lewis and A. M. Klibanov, *Trends in Biotech.,* 23, 7, 343-348 (2005)], destruction of an existing biofilm [P. Wood et al., *Appl. Env. Microb.* 62(7), 2598-2602 (1996)] and killing bacteria in biofilm [P. Gilbert and A. J. McBain, *Am. J. Infect. Control,* 29, 252-255 (2001)] are strategies towards lowering microbial load and reducing biofilm-related infection from any catheters and shunts, such as but not limited to, urinary and central venous catheters, implanted artificial joints, implanted artificial hearts, gastric feeding tubes, and colostomy tubes.

Compounds described herein may be used to treat, eradicate, or prevent the formation of biofilm formed by a variety of bacteria and fungi, including, but not limited to, gram-positive cocci, gram-negative rods, *P. aeruginosa, C. albicans, S. aureus, B. cepacia, E. coli, S. epidermidis, A. hydrophila, H. influenzae, S. liquifaciens, P. mirabilis, K. pneumoniae*, and *P. vulgaris*. A discussion of these, and examples of other, biofilm-forming species may be found in, e.g., S. Kjelleberg, and S. Molin, *Curr Opin Microbiol.*, June, 5(3):254-8 (2002); J. W. Consterton et al., *Science,* 284, May 21, 1318-11 (1999); and D. J. Stickler et al., *Methods in Enzymology,* 310: 494-501 (1999).

The starting materials and reagents employed in preparing the compounds described herein are either available from commercial suppliers such as Sigma-Aldrich Corporation (Milwaukee, Wis., USA), TCI America (Portland, Oreg., USA), Matrix Scientific (Columbia, S.C., USA), VWR International (Pasadena, Calif., USA), Fisher Scientific (Chicago, Ill., USA), Alfa Aesar (Ward Hill, Mass., USA), Advanced ChemTech (Louisville, Ky., USA), Chem-Impex International Inc. (Wood Dale, Ill., USA), and Advanced Asymmetrics (Millstadt, Ill., USA) or are prepared by methods known in the art following procedures available in the literature and references such as *Protective Groups in Organic Synthesis* (John Wiley & Sons, 3$^{rd}$ Edition), *Protective Groups (Foun-* dation of Organic Chemistry) (Thieme & Sons Inc.), Fieser and Fieser's Reagents for Organic Synthesis, Volumes 1-15 (John Wiley and Sons, 1991), Rodd's Chemistry of Carbon Compounds, Volumes 1-15 and Supplemental Materials (Elsevier Science Publishers, 1989), Organic Reactions, Volume 1-40 (John Wiley & Sons, 1991), March's Advanced Organic Chemistry, (Wiley-Interscience, 6$^{th}$ Edition, 2007), M. C. Pirrung, The Synthetic Organic Chemist's Companion (John Wiley & Sons, Inc., 2007), and R. C. Larock Comprehensive Organic Transformation: A Guide to Functional Group Preparations (John Wiley & Sons, Inc. 1999).

Various chlorine sources may be used to produce the N-chlorinated compounds, e.g., chlorine itself (i.e., $Cl_2$ gas), certain N-chloroarylsulfonamide salts, wherein the aryl group contains from about 6 to about 15 carbon atoms with 1 or 2 aromatic rings, or 6 to 10 or 6 to 8 carbon atoms and one aromatic ring, such as N-chlorobenzene-sulfonamide or N-chloro-4-alkylbenzenesulfonamide, wherein the alkyl group is an alkyl from about 1 to about 4 carbons, such as methyl or ethyl. The N-chlorobenzene-sulfonamides or N-chloro-4-alkylbenzenesulfonamides are often used in the form of their salts, e.g., alkali salts, e.g., sodium or potassium salts. Frequently used reagents include N-chlorobenzene-sulfonamide and N-chloro-4-methyl-benzenesulfonamide in the form of their sodium salts, because they are readily commercially available. Other non-limiting chlorinating agents include HOCl and N-chlorosuccinimide. Other chlorinated agents are listed in the schemes below. Similarly, the halogenation reaction may be accomplished using the corresponding reagents as disclosed herein that provide a source of bromine, as in known in the art. Examples of such bromination reagents include $Br_2$, N-bromoarylsulfonamide salts, HOBr and N-bromosuccinimide, and the like.

Compounds of Formula I may be prepared according to the following exemplary generalized schemes in addition to other standard manipulations known in the art. These schemes are illustrative and are not limiting. Compound numbers shown in the schemes do not necessarily correlate to compound numbers used in Table 1 or the Examples.

Scheme 1:

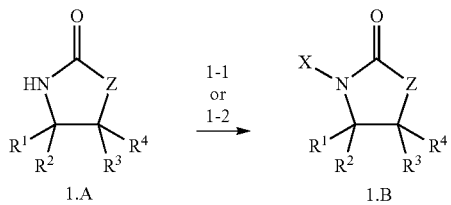

Step 1-1: The secondary nitrogen of an oxazolidin-2-one (Z=O), imidazolidin-2-one (Z=NR$^5$), or a pyrrolidin-2-one (Z=CH$_2$), can be N-chlorinated by the treatment with a chlorinating agent such as tert-butyl hypochlorite, trichloroisocyanuric acid, sodium hypochlorite, N-chlorosuccinimide, N-chlorohydantoins and chlorine gas in a polar solvent such as water, methanol, N,N-dimethylformamide, methylene chloride and the like to give N-chloro species 1.B. The reaction is typically carried out at low temperature to ambient temperature.

Step 1-2: The secondary nitrogen of an oxazolidin-2-one, imidazolidin-2-one, or a pyrrolidin-2-one (1.A), can be N-brominated by the treatment with a brominating agent such as bromine, hypobromous acid, N-bromosuccinimide, bromate, and tert-butylhypobromite in a polar solvent such as water, dilute sodium hydroxide, methanol, N,N-dimethylformamide, methylene chloride and the like to give N-bromo species 1.B. The reaction is typically carried out at low temperature to ambient temperature.

Scheme 2:

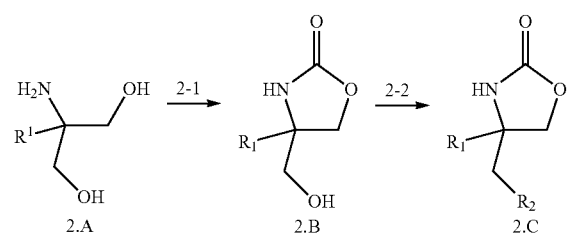

Step 2-1: Oxazolidin-2-ones 2.B may be prepared by heating an amino alcohol 2.A in neat diethyl carbonate at 100-150° C. for several hours, using a Dean-Stark trap to collect the ethanol generated by the reaction. Optionally a base such as potassium carbonate or triethylamine can be added. See also M. Murakata et al., Organic Letters 2001, 3, 299-302.

Step 2-2: Halomethyl oxazolidinones 2.0 may be prepared from the corresponding alcohol 2.B by treatment with dehydrative halogenating reagents such as, but not limited to, diethylaminosulfur trifluoride (DAST), thionyl chloride with pyridine, phosphorous oxychloride, phosphorous pentachloride, phosphorous trichloride, triphenylphosphine with N-chlorosuccinamide, triphenylphosphine with carbon tetrabromide, or phosphorous tribromide in a solvent such as dichloroethane under elevated temperatures. Alternatively, halomethyl oxazolidinones can be interconverted by treatment of a halomethyl oxazolidinone 2.0 with a halide source such as sodium fluoride, sodium chloride, potassium chloride, sodium bromide, or potassium bromide in a polar aprotic solvent such as N,N-dimethylformamide or tetrahydrofuran, optionally with the addition of a crown ether such as 12-crown-4 or 18-crown-6.

Scheme 3:

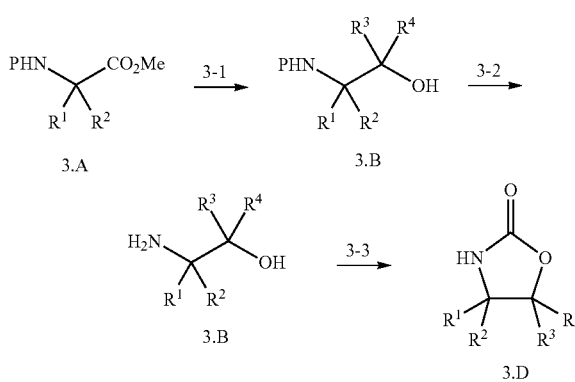

Step 3-1: An amino alcohol may be prepared from the corresponding protected amino acid derivative using a reducing agent such as sodium borohydride, lithium borohydride, lithium aluminum hydride, sodium triacetoxyborohydride, or an organometallic reagent such as methyl lithium, ethylmagnesium bromide in an aprotic solvent such as tetrahydrofuran or diethyl ether.

Step 3-2: The N-protecting group on the amino alcohol can be removed using references found in Greene and Wuts, *Protective Groups in Organic Synthesis* (Wiley-Interscience, 1999).

Step 3-3: Oxazolidinones 3.D can be synthesized by the treatment of amino alcohols 3.0 with a chloroformate such as ethyl chloroformate or benzyl chloroformate, followed by treatment with a base such as sodium hydroxide or triethylamine in either a solvent such as dichloromethane or water or a vigorously stirred solution of two solvents such as dichloromethane and water.

Scheme 4:

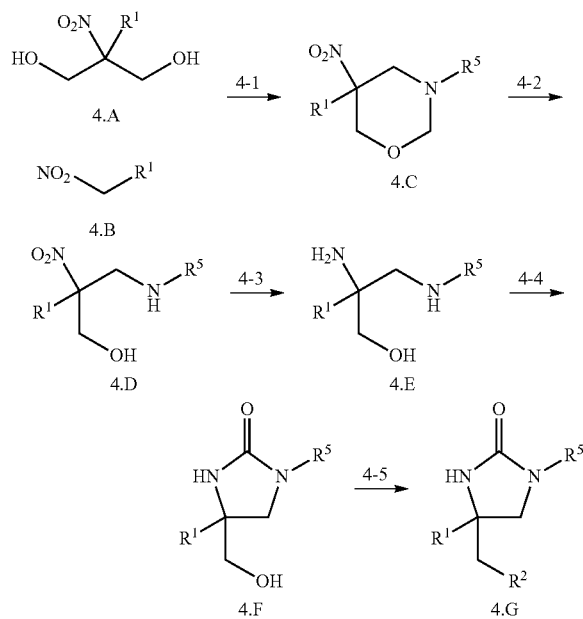

Step 4-1: Various 1,3-oxazinane compounds (4.C) may be prepared by literature methods (e.g. Urbanski, T., *Synth.*, 1974, 613-632) or variations thereof, wherein a 2-nitro-1,3-propane-diol based compound (4.A) is reacted with an aldehyde, such as formaldehyde, and an amine to produce a 1,3-oxazinane through a retro-aldol/Mannich type reaction. Alternatively, compound 4.0 may be produced by reaction of an appropriate nitro-alkane (4.B) with formaldehyde and the desired amine.

Step 4-2: Hydrolysis of the 1,3-oxazinane 4.0 may be accomplished by acid catalysis, preferably using hydrochloric acid in ethanol-water at refluxing temperatures for 4-16 hours, to ring open to the desired nitro-aminoalcohol 4.D. Alternative conditions are expected to accomplish the same transformation, for example but not limited to, using HBr, $H_2SO_4$, or TFA in solvents such as, but not limited to, water, alcohol and aqueous alcohols at various temperatures.

Alternatively, in some cases, compounds of type 4.D may also be produced directly from compounds of type 4.A without going through an oxazine intermediate by reaction with the appropriate amine, $H_2NR^5$, in solvents such as methanol or dioxane.

Step 4-3: The diamine 4.E may be produced by the reduction of the nitro group, which is preferably accomplished by a Raney-Ni catalyzed hydrogenation run at 450 psi $H_2$ in methanol for 48 hours. Alternatively this step may use other reductive conditions such as hydrogenation with palladium catalysis, or treatment with lithium aluminum hydride, activated sodium borohydride, iron-HCl, zinc-HCl, sodium sulfide, or other reagents known in the art for reduction of aliphatic nitro groups to amines including, but not limited, to those described in Larock's *Comprehensive Organic Transformations* (VCH Publishers Inc., 1989).

Step 4-4: The 2-imidazolidinone 4.F may be prepared by directly reacting the diamine 4.E, or a salt thereof, with urea under elevated temperatures, such as heating the neat mixture at ca 200° C. until ammonia evolution ceases. Alternatively this transformation may be accomplished by treatment of the diamine with triphosgene, phosgene, or 1,1'-carbonyldiimidazole in the appropriate solvent with base as necessary.

Step 4-5: The primary hydroxyl group of compound 4.F may be transformed into the desired functional group R2 either directly or through an intermediate R2 species. In the case where the desired R2 is Cl, the hydroxyl group can be converted to the chloride by treatment with thionyl chloride and pyridine in a solvent such as dichloroethane under elevated temperatures. Alternatively a variety of reagents known in the art can affect the transformation of alcohol to chloride including, but not limited to, phosphorous oxychloride, phosphorous pentachloride, phosphorous trichloride, triphenylphosphine with N-chlorosuccinamide, and triphenylphosphine with carbon tetrachloride. Alternatively, halomethyl imidazolidinones can be interconverted by treatment of a chloromethyl imidazolidinone 4.G with a halide source such as sodium fluoride, sodium bromide, or potassium bromide in a polar aprotic solvent such as N,N-dimethylformamide or tetrahydrofuran, optionally with the addition of a crown ether such as 12-crown-4 or 18-crown-6.

Scheme 5:

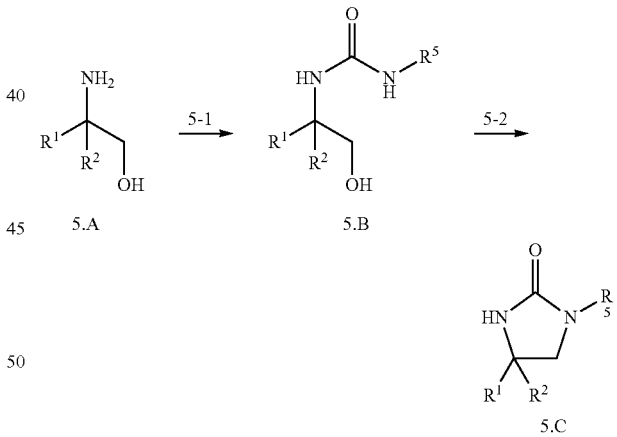

Step 5-1: Ureas, such as compound 5.B, can be formed by reaction of amino alcohols or amino-diols, in the case where $R^2$ is a hydroxymethyl, with an appropriate isocyanate. Typically these reactions can be run at room temperature for 8 to 16 hours in solvents such as THF, DMF, or mixtures thereof.

Step 5-2: 2-Imidazolidinones (5.C) can be formed by treating the urea 5.B with the appropriate halogenating reagents under conditions which promote cyclization. For example, typically treatment of 5.B with triphenylphosphine and carbon tetrabromide in anhydrous pyridine at 65° C. for 5 hours results in cyclization to the imidazolidinone. In cases where R2 is a hydroxymethyl, this also transforms R2 into a bromomethyl, which can be further transformed into other functional groups as desired. Using alternative halogenating or alcohol activating agents, such as but not limited to triphenylphosphine with carbon tetrabromide or triphenylphosphine with N-chlorosuccinamide, allows synthesis of 2-imidazolidinones with $R^2$ as the chloromethyl.

Scheme 6:

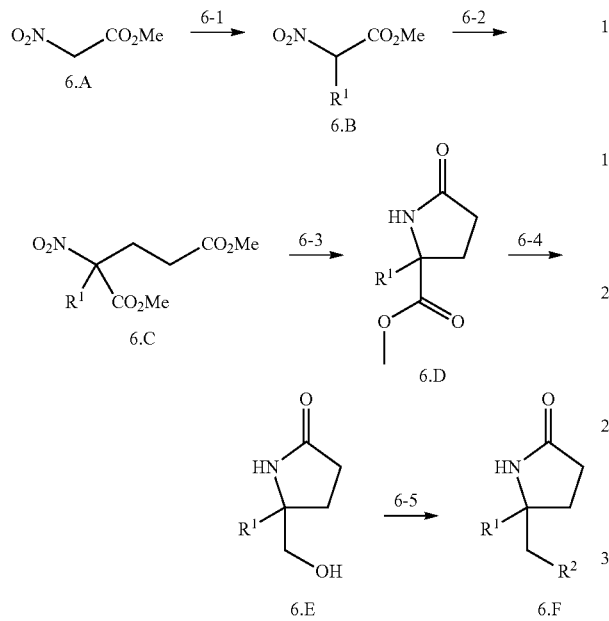

Step 6-1: Methyl 2-nitroacetate (6.A) can be deprotonated with a mild base such as triethylamine or diisopropylethylamine, and alkylated using a variety of methods, including but not limited to, $S_N2$ displacement with an alkyl halide, Michael addition into a vinyl sulfone, π-allylation with a palladium π-allyl complex, and condensation with an aldehyde such as benzaldehyde followed by hydrogenation, to give the monoalkylated nitroacetate 6.B.

Step 6-2: Monoalkylated nitroacetate 6.B can be deprotonated with a mild base such as triethylamine or diisopropylethylamine and alkylated with methyl acrylate, preferably in a polar solvent such as methanol or ethanol at reflux temperature.

Step 6-3: Reduction of the nitro group is preferably accomplished with Raney Nickel at 450 psi of hydrogen, and the intermediate amine produced spontaneously closes to form the pyrrolidin-2-one 6.D.

Step 6-4: The methyl ester of 6.D is reduced to a hydroxymethyl group using a reducing agent such as lithium borohydride, lithium aluminum hydride, or sodium borohydride.

Step 6-5: Halomethyl pyrrolidin-2-ones 6.F may be prepared from the corresponding alcohol 6.E by treatment with dehydrative halogenating reagents such as, but not limited to, diethylaminosulfur trifluoride (DAST), thionyl chloride with pyridine, phosphorous oxychloride, phosphorous pentachloride, phosphorous trichloride, triphenylphosphine with N-chlorosuccinamide, triphenylphosphine with carbon tetrabromide, or phosphorous tribromide in a solvent such as dichloroethane under elevated temperatures. Alternatively, halomethyl pyrrolidinones can be interconverted by treatment of a halomethyl oxazolidinone 6.F with a halide source such as sodium fluoride, sodium chloride, potassium chloride, sodium bromide, or potassium bromide in a polar aprotic solvent such as N,N-dimethylformamide or tetrahydrofuran, optionally with the addition of a crown ether such as 12-crown-4 or 18-crown-6.

EXAMPLES

The following examples are offered by way of illustration and not by way of limitation.

Example 1

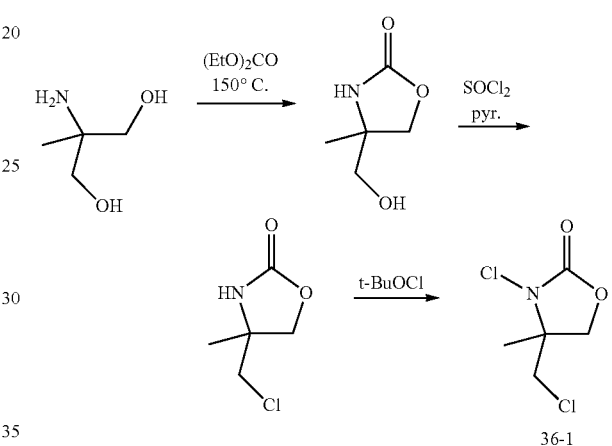

Synthesis of 3-chloro-4-(chloromethyl-4-methyloxazolidin-2-one (Compound 36-1)

4-(Hydroxymethyl)-4-methyloxazolidin-2-one

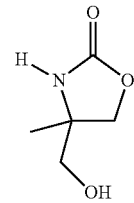

A Dean-Stark trap was fitted to a flask containing 2-amino-2-methyl-1,3-propanediol (21.62 g, 205.6 mmol) suspended in diethyl carbonate (40 ml, 330 mmol). The suspension was heated to 150° C. for 6 h, during which time approximately 12 ml of ethanol was distilled. The solution was cooled to RT overnight, and the resulting crystals were filtered and washed with cold ethanol. The crude material (~90% purity) was used without further purification (24.82 g, 189.0 mmol, 92%). $^1$H NMR (CDCl$_3$, 400 MHz) δ 1.36 (s, 3H), 2.2 (br s, 1H), 3.57 (m, 2H), 4.06 (d, 1H, J=8.8 Hz), 4.33 (d, 1H, J=8.8 Hz), 5.2 (br s, 1H). LRMS (ESI/APCI): 132 [M+H]$^+$.

4-(Chloromethyl)-4-methyloxazolidin-2-one

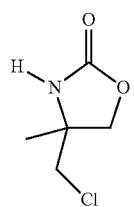

To a suspension of 4-(hydroxymethyl)-4-methyloxazolidin-2-one (1.89 g, 14.4 mmol) in 1,2-dichloroethane (10 ml) was added thionyl chloride (5.0 ml, 69 mmol). The solution was stirred for 30 min at RT, and then pyridine (5.0 ml, 62 mmol) was added. The solution was heated to 90° C. for 16 h and then 110° C. for an additional 2 h, then cooled to RT and evaporated. The residue was purified by flash chromatography (30% to 100% ethyl acetate in hexanes, $R_f$=0.25 in 1:1 ethyl acetate:hexanes) to give the title compound as a clear oil which solidified to a white solid upon standing (1.52 g, 10.2 mmol, 71%). $^1$H NMR (CDCl$_3$, 400 MHz) δ 1.49 (s, 3H), 3.55 (m, 2H), 4.12 (d, 1H, J=9.2 Hz), 4.31 (d, 1H, J=8.8 Hz), 5.4 (br s, 1H). LRMS (ESI/APCI): 150 [M+H]$^+$.

3-Chloro-4-(chloromethyl)-4-methyloxazolidin-2-one

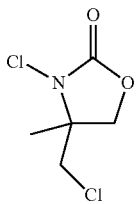

A solution of 4-(chloromethyl)-4-methyloxazolidin-2-one (13.39 g, 89.52 mmol) in MeOH (100 ml) was cooled to 0° C., and tert-butylhypochlorite (12.0 ml, 101 mmol) was added dropwise over 15 min. The solution was warmed to RT over 45 min, and concentrated in vacuo. The residue was crystallized by dissolution in ~80 ml CH$_2$Cl$_2$ followed by careful layering of 60 ml hexanes to afford the title compound as white, fan-shaped crystals (12.31 g, 66.89 mmol, 75%). $^1$H NMR (CDCl$_3$, 400 MHz) δ1.50 (s, 3H), 3.55 (d, J=12.0 Hz, 1H), 3.75 (d, J=12.0 Hz, 1H), 4.19 (d, J=8.8 Hz, 1H), 4.53 (d, J=8.4 Hz, 1H). $^{13}$C NMR (CDCl$_3$, 100 MHz) δ 20.4, 46.7, 64.1, 155.7. LRMS (ESI/APCI): 225 [M+H+CH$_3$CN]$^+$, 191 [M+H–Cl+CH$_3$CN]$^+$, 184 [M+H]$^+$, 150 [M+H–Cl]$^+$.

Example 2

Synthesis of 3-chloro-4-(chloromelhyl)-1,4-dimclhylimida/olidin-2-one (Compound 36-2)

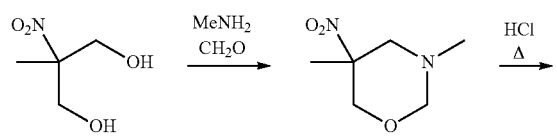

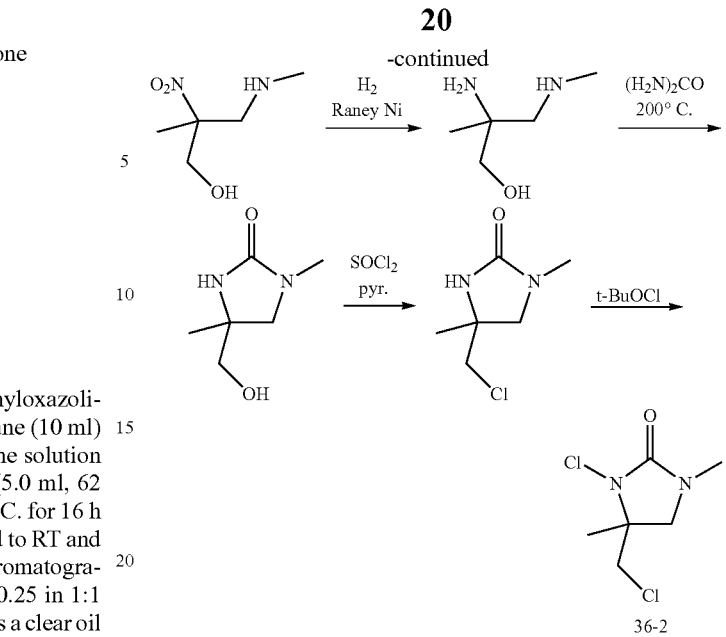

3,5-Dimethyl-5-nitro-1,3-oxazinane

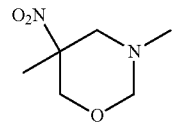

To a solution of 2-nitro-2-methyl-1,3-propanediol (20.4 g, 151 mmol) in 40% aqueous methylamine (11.7 g, 151 mmol), was added an aqueous solution of formaldehyde (37%, 12.2 g, 151 mmol). The reaction was stirred at room temperature for one week, then extracted with ether three times. The organic fractions were dried over sodium sulfate and concentrated under reduced pressure to give a crude oil which was purified by column chromatography, eluting from silica gel with a gradient of 50-100% ethyl acetate in hexanes to give 15.4 g of desired product (63% yield). $^1$H NMR (400 MHz, CDCl$_3$) δ 1.45 (s, 3H), 2.32 (s, 3H), 2.63-2.66 (d, J=13.2 Hz, 1H), 3.51-3.54 (d, J=12.6 Hz, 1H), 3.67-3.71 (d of trip, J=1.9, 13.2 Hz, 1H), 3.86-3.89 (d, J=8.5 Hz, 1H), 4.29-4.32 (dd, J=1.2, 8.6 Hz, 1H), 4.61-4.66 (dd, J=2.4, 12.6 Hz, 1H). $^{13}$C NMR (100 MHz, CDCl$_3$) δ 22.0, 39.9, 59.8, 71.2, 83.1, 86.1. LRMS (ESI/APCI): 161[M+H]$^+$.

2-Methyl-3-(methylamino)-2-nitropropan-1-ol hydrochloride

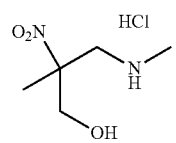

A solution of 3,5-dimethyl-5-nitro-1,3-oxazinane (11.5 g, 71.8 mmol) in 280 ml ethanol, 50 ml water, and 12 ml of concentrated hydrochloric acid was equipped with a dean stark trap and heated at reflux temperature. To the refluxing reaction was slowly added a solution of 280 ml ethanol and 50 ml water. The rate of addition of the solution was matched to the rate of distillation and removal of an equal volume of solvent over the course of ca. 2 hours. After 4 hours at reflux temperature, the remaining solvent was distilled off and the crude residue was lyophilized from water to give 14.1 g of white solid, which was used directly in the next step without further purification. $^1$H NMR (400 MHz, D$_2$O) δ 1.53 (s, 3H), 2.74 (s, 3H), 3.62-3.66 (d, J=14.6 Hz, 1H), 3.68-3.72 (d, J=14.6 Hz, 1H), 3.84-3.87 (d, J=12.5 Hz, 1H), 4.10-4.13 (d, J=12.5 Hz, 1H). $^{13}$C NMR (100 MHz, D$_2$O) δ 18.9, 34.4, 52.8, 66.2, 88.9. LRMS (ESI/APCI):149 [M+H]$^+$.

2-Amino-2-methyl-3-(methylamino)propan-1-ol hydrochloride

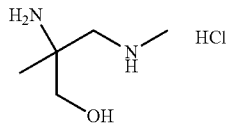

To a solution of 2-methyl-3-(methylamino)-2-nitropropan-1-ol hydrochloride (5.4 g) in MeOH (32 ml) was added a slurry of Raney Nickel in H$_2$O (1.5 ml). The vessel was pressurized with H$_2$ (450 psi) and the suspension stirred for 48 h. The mixture was filtered through Celite and concentrated in vacuo to give 7.4 g of a crude liquid, which was used directly in the next step without purification. $^1$H NMR (400 MHz, CDCl$_3$) δ 1.01 (s, 3H), 2.26 (s, 3H), 2.99 (s, 2H), 3.41-3.44 (d, J=11.6 Hz, 1H), 3.48-3.51 (d, J=11.6 Hz, 1H). LRMS (ESI/APCI): 145 [M+H]$^+$.

4-(Hydroxymethyl)-1,4-dimethylimidazolidin-2-one

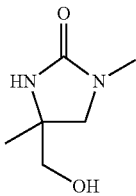

In a round bottom flask, a mixture of 2-amino-2-methyl-3-(methylamino)propan-1-ol hydrochloride (3.3 g, 21 mmol) and urea (1.26 g, 21 mmol) were heated in a 200° C. sand bath for 1 hour until ammonia gas ceased to evolve. The resultant mixture was suspended in dichloromethane and filtered to remove insoluble material. The organic solution was concentrated to 3.3 g of black solid and purified by column chromatography, eluting from silica gel with a gradient of 1-12% methanol in dichloromethane to give 1.3 g of desired product as a tan oil (45% yield). $^1$H NMR (400 MHz, CDCl$_3$) δ1.26 (s, 3H), 2.76 (s, 3H), 3.07-3.9 (d, J=8.8 Hz, 1H), 3.36-3.36 (d, J=8.8 Hz, 1H), 3.43-3.44 (d, J=2.1 Hz, 2H), 3.46 (s, 1H). $^{13}$C NMR (100 MHz, CDCl$_3$/MeOD) δ 23.5, 30.1, 50.0, 55.7, 67.7, 161.9. LRMS (ESI/APCI): 145 [M+H]$^+$.

4-(Chloromethyl)-1,4-dimethylimidazolidin-2-one

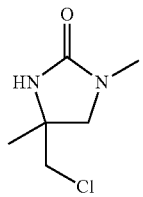

A solution of 4-(hydroxymethyl)-1,4-dimethylimidazolidin-2-one (3.3 g, 22.7 mmol), anhydrous pyridine (8.25 ml, 102 mmol), and thionyl chloride (8.26 ml, 114 mmol) in 46 ml of 1,2-dichloroethane was heated at reflux temperature for 8 hours. The reaction mixture was concentrated under reduced pressure, diluted with dichloromethane, and filtered to remove solids. The organic layer was washed with once 2 N HCl, which was back-extracted three times with dichloromethane, and the combined organic fractions were dried over sodium sulfate and concentrated to 2.2 g of yellow oil. The crude product was purified by column chromatorgraphy, eluting from silica gel with a gradient of 0-10% methanol in dichloromethane to give 897 mg of desired product as a white solid (25% yield). $^1$H NMR (400 MHz, CDCl$_3$) δ 1.42 (s, 3H), 2.79 (s, 3H), 3.17-3.20 (d, J=9.2 Hz, 1H), 3.36-3.39 (d, J=9.2 Hz, 1H), 3.50 (s, 2H). $^{13}$C NMR (100 MHz, CDCl$_3$) δ 24.2, 30.3, 51.5, 55.0, 57.0, 160.6. LRMS (ESI/APCI): 163 [M+H]$^+$.

3-Chloro-4-(chloromethyl)-1,4-dimethylimidazolidin-2-one

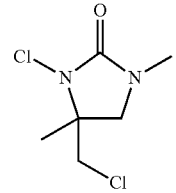

A solution of 4-(chloromethyl)-1,4-dimethylimidazolidin-2-one (204 mg, 1.25 mmol) in MeOH (2.5 ml) was cooled to 0° C. tert-Butylhypochlorite (177 ul, 1.57 mmol) was added. The resulting solution was stirred for 60 min, during which time a white precipitate formed. The reaction mixture was concentrated under reduced pressure to half its initial volume and the solid was collected on a glass fritted filter and washed with water to give 168 mg of desired product (69% yield). $^1$H NMR (400 MHz, CDCl$_3$) δ1.48 (s, 3H), 2.90 (s, 3H), 3.21-3.23 (d, J=8.8 Hz, 1H), 3.52-3.54 (d, J=8.9 Hz, 1H), 3.59-3.67 (q, J=11.1 Hz, 2H). $^{13}$C NMR (100 MHz, CDCl$_3$) δ 19.9, 31.7, 47.6, 54.5, 63.1, 158.7. LRMS (ESI/APCI): 197 [M+H]$^+$.

Example 3

Synthesis of 1-chloro-5-(chloromethyl)-5-methylpyrrolidin-2-one (Compound 36-3)

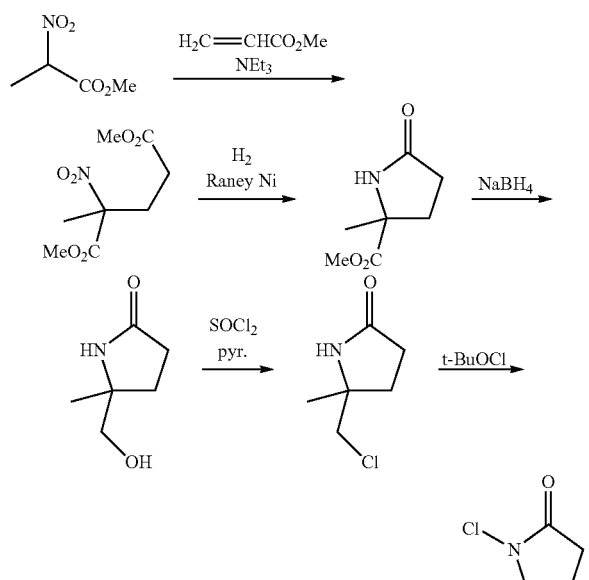

Methyl 2-methyl-5-oxopyrrolidine-2-carboxylate

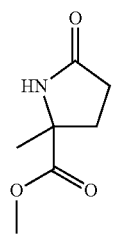

The compound was prepared as described in European Patent No. 438,311: A solution of methyl 2-nitropropionate (9.32 g, 70 mmol) in methanol (50 mL) was cooled to 0° C., whereupon neat triethylamine (0.5 mL, 3.5 mmol, 5 mol %) and neat methyl acrylate (6.6 mL, 73.5 mmol, 1.05 equiv.) were added sequentially. The mixture was stirred at 0° C. for an additional 10 mins, then warmed to room temperature and stirred overnight. After 16 h, the mixture was heated at reflux for 27 h, then concentrated in vacuo to afford the intermediate nitro-diester as a yellow oil (14.8 g, 97%), which was used directly in the next reaction. $^1$H NMR (400 MHz, CDCl$_3$) δ 3.83 (s, 3H), 3.71 (s, 3H), 2.65-2.46 (m, 2H), 2.45-2.36 (m, 2H), 1.81 (s, 3H). A solution of the dimethyl 2-methyl-2-nitropentanedioate (14.8 g, assumed 70 mmol) in methanol (50 mL) was treated with Raney nickel slurry (2.1 g, 50% in water), and the mixture hydrogenated at atmospheric pressure for 19 h, then at 500 psi for 68 h. The mixture was filtered through celite, and concentrated to a brown oil, which was absorbed on silica. Chromatography on silica (0-6% MeOH/DCM) afforded the lactam as a pale yellow oil, which solidified on standing (7.13 g, 63%). $^1$H NMR (400 MHz, CDCl$_3$) δ 6.23 (br, 1H), 3.78 (s, 3H), 2.59-2.51 (m, 1H), 2.42 (t, J=7.3 Hz, 2H), 2.09-2.00 (m, 1H), 1.54 (s, 3H); LRMS (ESI/APCI): 158 [M+H]$^+$.

5-(Hydroxymethyl)-5-methylpyrrolidin-2-one

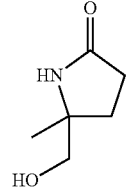

Solid sodium borohydride (3.2 g, 80 mmol, 2 equiv.) was added portionwise over 15 mins to a solution of methyl 2-methyl-5-oxopyrrolidine-2-carboxylate (6.68 g, 42.5 mmol) in ethanol (100 mL) After an additional 30 min, further sodium borohydride (1.6 g, 40 mmol, 1 equiv.) was added over 5 min, and the mixture was stirred overnight at room temperature. After 21 h, the foamy mixture was quenched with water (20 mL), and the solution decanted from the gummy white residue. The residue was triturated with methanol (50 mL), DCM (50 mL) and methanol (50 mL), during which time it became granular. The combined solutions were concentrated in vacuo, and the residue absorbed on silica. Chromatography on silica (0-8% MeOH/DCM) afforded the hydroxymethyl-pyrrolidinone as a white solid (4.85 g, 88%). $^1$H NMR (400 MHz, CDCl$_3$) δ 7.12 (br s, 1H), 4.20 (t, J=6.0 Hz, 1H), 3.50 (dd, J=5.7, 11.5 Hz, 1H), 3.44 (dd, J=7.1, 11.5 Hz, 1H), 2.52-2.45 (m, 2H), 2.10 (ddd, J=5.6, 9.8, 13.0 Hz, 1H), 1.86-1.78 (m, 1H), 1.26 (s, 3H); $^{13}$C NMR (100 MHz, CDCl$_3$) δ 178.8 (C), 69.5 (CH$_2$), 61.25 (CH$_2$), 31.135 (CH$_2$), 30.305 (CH$_2$), 24.25 (CH$_3$); LRMS (ESI/APCI): 130 [M+H]$^+$.

5-(Chloromethyl)-5-methylpyrrolidin-2-one

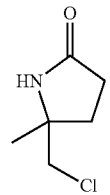

A 50 mL flask was charged with 5-(hydroxymethyl)-5-methylpyrrolidin-2-one (646 mg, 5 mmol), purged with nitrogen, and dry 1,2-dichloroethane (10 mL) and pyridine (1.8 mL, 22.5 mmol, 4.5 equiv.) were added. Neat thionyl chloride (1.8 mL, 25 mmol, 5 equiv.) was added dropwise over 10 min, during which the suspension clarified briefly before becoming a thick slurry. The mixture was stirred at room temperature for 30 min, then heated to reflux. After 3.5 h, the cooled mixture was concentrated to an orange semi-solid, which was absorbed on silica. Chromatography on silica (50-100% EtOAc/hexane) afforded the title compound as a colorless oil which solidified on standing (383 mg, 52%). $^1$H NMR (400 MHz, CDCl$_3$) δ 6.48 (br s, 1H), 3.52 (s, 2H), 2.56-2.41 (m, 2H), 2.15 (ddd, J=6.0, 9.4, 15.4 Hz, 1H), 1.98 (ddd, J=7.9, 9.4, 17.3 Hz, 1H), 1.42 (s, 3H); LRMS (ESI/APCI): 148 [M+H]$^+$.

1-Chloro-5-(chloromethyl)-5-methylpyrrolidin-2-one

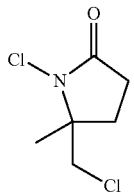

A solution of 5-(chloromethyl)-5-methylpyrrolidin-2-one (302 mg, 2.05 mmol) in methanol (20 mL) was cooled in ice water for 10 min, before neat tert-butyl hypochlorite (0.46 mL, 4.1 mmol, 2 equiv.) was added in one portion. Additional tert-butyl hypochlorite (0.46 mL, 4.1 mmol, 2 equiv.) was added after 45 min. After 1 h, the mixture was concentrated in vacuo and the residue absorbed on silica. Chromatography on silica (0-2.5% MeOH/DCM) afforded the N-chloro-pyrrolidinone as a colorless oil (292 mg, 78%). $^1$H NMR (400 MHz, CDCl$_3$) δ 3.74 (d, J=11.9 Hz, 1H), 3.50 (J=11.9 Hz, 1H), 2.66-2.57 (m, 1H), 2.54-2.40 (m, 2H), 2.10-2.01 (m, 1H), 1.43 (s, 3H); $^{13}$C NMR (100 MHz, CDCl$_3$) δ171.6 (C), 65.4 (C), 49.1 (CH$_2$), 28.9 (CH$_2$), 27.8 (CH$_2$), 23.1 (CH$_3$); LRMS (ESI/APCI): 182 [M+H]$^+$.

Example 4

Synthesis of 3-bromo-4-(chloromethyl)-4-methyloxazolidin-2-one (Compound 36-4)

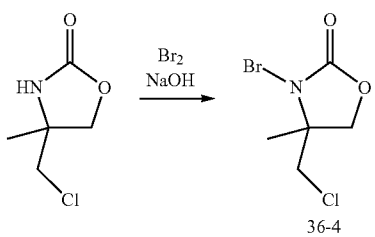

A solution of 4-(chloromethyl)-4-methyloxazolidin-2-one (2.70 g, 18.1 mmol) in 1.0 M NaOH (20 ml) was cooled to 0° C. Bromine (1.0 ml, 20 mmol) was added dropwise, and stirred for 30 min. The precipitate was filtered off to give the title compound (2.32 g, 10.2 mmol, 56%). $^1$H NMR (CDCl$_3$, 400 MHz) δ 1.44 (s, 3H), 3.49 (d, J=12.0 Hz, 1H), 3.65 (d, J=12.0 Hz, 1H), 4.22 (d, J=8.8 Hz, 1H), 4.57 (d, J=8.4 Hz, 1H). LRMS (ESI/APCI): 228 [M+H]$^+$.

Example 5

Synthesis of 4-(bromomethyl)-3-chloro-4-methyloxazolidin-2-one (Compound 36-5)

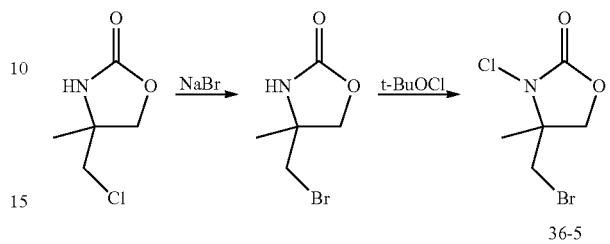

4-(Bromomethyl)-4-methyloxazolidin-2-one

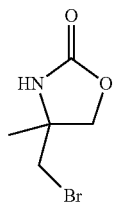

To a solution of 4-(chloromethyl)-4-methyloxazolidin-2-one (1.49 g, 9.96 mmol) in DMF (100 ml) was added sodium bromide (11.02 g, 107 mmol), and the suspension heated to 80° C. for 6 h. The suspension was concentrated in vacuo and the residue purified by flash chromatography (30% to 60% ethyl acetate in hexanes) to give the title compound as a white solid (1.33 g, 6.86 mmol, 66%). $^1$H NMR (CDCl$_3$, 400 MHz) δ 1.54 (s, 3H), 3.47 (s, 2H), 4.14 (d, J=9.2 Hz, 1H), 4.35 (d, J=8.8 Hz, 1H), 6.24 (br s, 1H). LRMS (ESI/APCI): 194 [M+H]$^+$.

4-(Bromomethyl)-3-chloro-4-methyloxazolidin-2-one

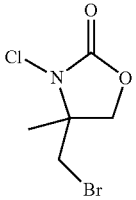

A solution of 4-(bromomethyl)-4-methyloxazolidin-2-one (1.33 g, 6.86 mmol) in MeOH (10 ml) was cooled to 0° C. and tert-butylhypochlorite (1.0 ml, 8.4 mmol) as added dropwise. The solution was stirred for 30 min, concentrated in vacuo, and the residue purified by flash chromatography (20% to 60% ethyl acetate in hexanes) to afford the title compound as a white solid (960 mg, 4.20 mmol, 61%). $^1$H NMR (CDCl$_3$, 400 MHz) δ 1.57 (s, 3H), 3.45 (d, J=10.4 Hz, 1H), 3.60 (d, J=10.8 Hz, 1H), 4.20 (d, J=8.8 Hz, 1H), 4.51 (d, J=8.8 Hz, 1H). LRMS (ESI/APCI): 228 [M+H]$^+$.

Example 6

Synthesis of 3-chloro-4,4-bis(chloromethyl)oxazolidin-2-one (Compound 36-6)

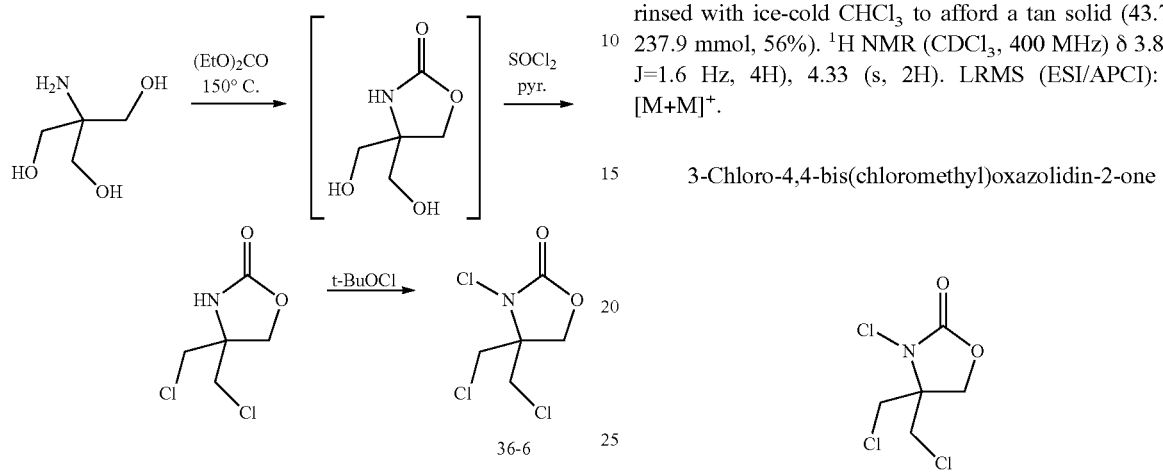

4,4-Bis(hydroxymethyl)oxazolidin-2-one

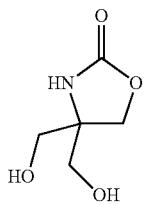

A suspension of 2-amino-2-(hydroxymethyl)propane-1,3-diol (51.37 g, 424.1 mmol) in diethyl carbonate (55 ml) was heated to 140° C. for 14 h, during which approximately 50 ml of ethanol was collected in a Dean-Stark trap. The reaction mixture was cooled to RT and the resulting thick, clear syrup was used without further purification. LRMS (ESI/APCI): 148 [M+H]+.

4,4-Bis(chloromethyl)oxazolidin-2-one

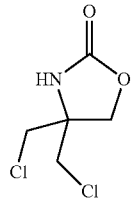

To a suspension of 4,4-bis(hydroxymethyl)oxazolidin-2-one (424.1 mmol) in pyridine (300 ml, 3.7 mol) was added, slowly (ca. over 1 h), thionyl chloride (300 ml, 4.1 mol) at a rate which kept the solution hot but not boiling. The solution was then heated to 110° C. for 3 h, cooled to RT, and poured slowly into a vigorously stirred, ice-cold sat. NaHCO$_3$ solution, with Na$_2$CO$_3$ powder added to maintain the pH at ca. 9. The slurry was extracted with 5×300 ml EtOAc, the organic phases combined and washed with 500 ml sat. NaCl, dried on MgSO$_4$, and concentrated in vacuo. The residue was suspended in ca. 200 ml CH$_2$Cl$_2$, and filtered. The filter cake was rinsed with ice-cold CHCl$_3$ to afford a tan solid (43.77 g, 237.9 mmol, 56%). $^1$H NMR (CDCl$_3$, 400 MHz) δ 3.81 (d, J=1.6 Hz, 4H), 4.33 (s, 2H). LRMS (ESI/APCI): 184 [M+M]+.

3-Chloro-4,4-bis(chloromethyl)oxazolidin-2-one

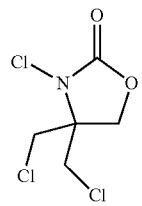

To a solution of 4,4-bis(chloromethyl)oxazolidin-2-one (1.11 g, 6.03 mmol) in MeOH (10 ml) was added tert-butylhypochlorite (1.0 ml, 8.4 mmol). The solution was stirred for 1 h, concentrated in vacuo, and the residue purified by flash chromatography (30% to 80% EtOAc in hexanes) to afford the title compound as a white solid (1.04 g, 4.76 mmol, 79%). $^1$H NMR (CDCl$_3$, 400 MHz) δ 3.78 (d, J=12.0 Hz, 2H), 3.84 (d, J=12.4 Hz, 2H), 4.55 (s, 2H). LRMS (ESI/APCI): 228 [M+H]+.

Example 7

Synthesis of 3-chloro-4-(fluoromethyl)-4-methyl-oxazolidin-2-one (Compound 36-7)

2-amino-3-fluoro-2-methylpropanoic acid

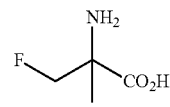

Potassium cyanide (8.46 g, 130 mmol), ammonium chloride (6.97 g, 130 mmol), and fluoroacetone (9.91 g, 130 mmol) were dissolved in water (130 ml) and stirred for 18 h. The solution was basified with 50% NaOH to pH 11, extracted with diethyl ether, the organic phases combined, dried on Na$_2$SO$_4$, and concentrated in vacuo to afford the title compound as a clear liquid (7.6 g). $^1$H NMR (CDCl$_3$, 400 MHz) δ 1.49 (s, 3H), 2.00 (br s, 2H), 4.22 (d, J=10.4 Hz, 0.5H), 4.34 (dd, J=9.2, 3.6 Hz, 1H), 4.46 (d, J=8.8 Hz, 0.5H). $^{19}$F NMR (CDCl$_3$, 376 MHz) δ 16.4 (t, J=46.2 Hz).

2-(benzyloxycarbonylamino)-3-fluoro-2-methylpropanoic acid

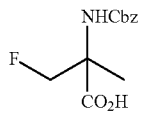

A solution of 2-amino-3-fluoro-2-methylpropanenitrile (7.6 g, 74.5 mmol) in 6 M HCl (250 ml, 1.5 mol) was heated to reflux for 22 h, then concentrated in vacuo, to afford 2-amino-3-fluoro-2-methylpropanoic acid which was dissolved in MeOH (170 ml) and triethylamine (30 ml). CbzOSu (34 g, 138 mmol) was added, and the suspension stirred for 24 h, concentrated in vacuo, the residue partitioned between EtOAc and 1 M HCl, and the organic phase dried over $Na_2SO_4$ and concentrated in vacuo. The residue was purified by flash chromatography (1% to 10% MeOH in DCM) to afford 2-(benzyloxycarbonylamino)-3-fluoro-2-methylpropanoic acid as a tan oil (9.35 g). LRMS (ESI/APCI, negative): 254 [M−H$^+$].

benzyl 1-fluoro-3-hydroxy-2-methylpropan-2-ylcarbamate

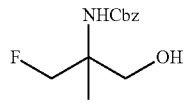

A solution of 2-(benzyloxycarbonylamino)-3-fluoro-2-methylpropanoic acid (1.1 g, 4.9 mmol) in THF (16 ml) was cooled to 0° C., and triethylamine (518 mg, 6.1 mmol) was added, then ethyl chloroformate (663 mg, 6.11 mmol). A solution of sodium borohydride (370 mg, 9.8 mmol) in water (4 ml) was added, and the reaction warmed to RT over 4 h. The reaction was quenched with 1 M HCl, and extracted with EtOAc. The organic layers were combined, washed with sat. NaCl, dried on $Na_2SO_4$, and concentrated in vacuo. Flash chromatography (0% to 10% MeOH in DCM) afforded the title compound as a clear oil (915 mg, 77%). $^1$H NMR (CDCl$_3$, 400 MHz) δ 1.31 (s, 3H), 3.4 (br s, 1H), 3.72-3.80 (m, 2H) 4.47 (dd, J=9.6, 18.4 Hz, 1H), 4.60 (dd, J=9.2, 18.8 Hz, 1H), 5.12 (s, 2H), 5.32 (s, 1H), 7.28-7.37 (m, 5H). $^{19}$F NMR (CDCl$_3$, 376 MHz) δ −231.2 (t, J=48.9 Hz). $^{13}$C NMR (CDCl$_3$, 100 MHz) δ 19.2 (d, J=4 Hz), 56.8 (d, J=17 Hz), 66.4 (d, J=4 Hz), 66.9, 85 (d, J=173 Hz), 128.1, 128.3, 128.6, 128.6, 136.0, 156.0.

4-(fluoromethyl)-4-methyloxazolidin-2-one

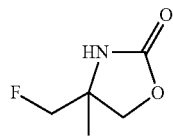

A solution of benzyl 1-fluoro-3-hydroxy-2-methylpropan-2-ylcarbamate (562 mg, 2.3 mmol) in THF (29 ml) was cooled to 0° C. and 60% NaH in mineral oil (117 mg, 2.9 mmol) was added. The reaction was warmed to RT over 3 h, and then heated to 50° C. for 16 h. AcOH (200 ul) was added to quench the reaction, and the solution was concentrated in vacuo. The residue was purified by flash chromatography (1% to 12% MeOH in DCM) to afford the title compound as a clear oil (251 mg, 82%). $^1$H NMR (CDCl$_3$, 400 MHz) δ 1.40 (d, J=2.0 Hz, 3H), 4.08 (dd, J=2.0, 8.8 Hz, 1H), 4.24 (dd, J=9.6, 20.4 Hz, 1H), 4.32-4.40 (m, 2H), 6.61 (s, 1H). $^{19}$F NMR (CDCl$_3$, 376 MHz) δ −225.4 (t, J=47 Hz). $^{13}$C NMR (CDCl$_3$, 100 MHz) δ 21.7 (d, J=3 Hz), 67.4 (d, J=20 Hz), 72.3 (d, J=4.2 Hz), 86 (d, J=178 Hz), 159.3 (s).

3-chloro-4-(fluoromethyl)-4-methyloxazolidin-2-one

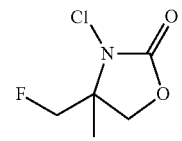

A solution of 4-(fluoromethyl)-4-methyloxazolidin-2-one (245 mg, 1.82 mmol) in MeOH (5 ml) was cooled to 0° C. and tert-butylhypochlorite (251 mg, 2.3 mmol) was added dropwise. The solution was stirred for 2 h, concentrated in vacuo, and the residue purified by flash chromatography (0% to 10% MeOH in DCM) to afford the title compound as a white solid (303 mg, 100%). $^1$H NMR (CDCl$_3$, 400 MHz) δ 1.38 (d, J=2.4 Hz, 3H), 4.22 (dd, J=1.2, 8.8 Hz, 1H), 4.24 (d, J=11.2 Hz, 0.5H), 4.35 (d, J=10.4 Hz, 0.5H), 4.53 (d, J=10.4 Hz, 0.5H), 4.54 (dd, J=0.8, 8.8 Hz, 1H), 4.64 (d, J=10.4 Hz, 0.5H). $^{19}$F NMR (CDCl$_3$, 376 MHz) δ −228.4 (t, J=84 Hz). $^{13}$C NMR (CDCl$_3$, 100 MHz) δ 17.7 (d, J=3.7 Hz), 63.5 (d, J=18 Hz), 70.7 (d, J=4 Hz), 82 (d, J=179 Hz), 155.8 (s). LRMS (ESI/APCI): 168 [M+H]$^+$, 209 [M+H+CH$_3$CN]$^+$.

Example 8

Synthesis of 3-chloro-4-(2,2,2-trifluoroethyl)-4-methyl-oxazolidin-2-one (Compound 36-8)

(R)-2-methyl-N-(4,4,4-trifluorobutan-2-ylidene)propane-2-sulfinamide

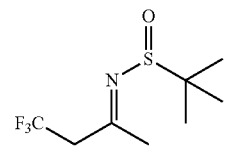

To a solution of 4,4,4-trifluorobutan-2-one (12 g, 95 mmol) in THF (150 ml) was added titanium (IV) isopropoxide (42 ml, 142 mmol) and (R)-tert-butanesulfinamide (17.3 g, 142 mmol). The solution was heated to reflux for 22 h, cooled to RT, and poured into a vigorously-stirred brine solution. The mixture was filtered through a pad of Celite, the filter cake washed with EtOAc, and the filtrate separated. The aqueous layer was extracted with EtOAc, the organic layers combined and washed with brine, dried on $Na_2SO_4$, and concentrated in vacuo. The residue was purified by column chromatography (15% to 60% EtOAc in hexanes) to afford the title compound as a yellow oil (14.0 g, 65%). $^1$H NMR (CDCl$_3$, 400 MHz) δ

1.25 (s, 9H), 2.45 (s, 3H), 3.19 (q, J=14.4 Hz, 2H). $^{19}$F NMR (CDCl$_3$, 376 MHz) δ -61.03 (t, J=10.5 Hz), -62.8 (t, J=10.5 Hz).

N-(2-cyano-4,4,4-trifluorobutan-2-yl)-2-methylpropane-2-sulfinamide

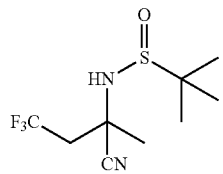 [SMILES: CC(C#N)(CC(F)(F)F)NS(=O)C(C)(C)C]

A solution of 1 M Et$_2$AlCN (92 ml, 92 mmol) in THF (150 ml) was cooled to -78° C. and isopropanol (4.7 ml, 61 mmol) was added. The solution was stirred and warmed to RT over 30 min, then cooled to -78° C. and added to a solution of (R)-2-methyl-N-(4,4,4-trifluorobutan-2-ylidene)propane-2-sulfinamide (14 g, 61 mmol) in THF (500 ml) cooled to -78° C. The combined solution was warmed to RT overnight, concentrated in vacuo, and quenched by the addition of sat. NH$_4$Cl. The suspension was filtered through Celite, and then extracted with EtOAc. The organic layers were combined, washed with sat. NaCl, dried on Na$_2$SO$_4$, and concentrated in vacuo. The residue was purified by flash chromatography to afford the title compound as a tan solid (7.7 g). $^1$H NMR (CDCl$_3$, 400 MHz) δ 1.28 (s, 9H), 1.94 (s, 3H), 2.71-2.87 (m, 2H), 3.77 (s, 1H). $^{19}$F NMR (CDCl$_3$, 376 MHz) δ -60.53 (t, J=10 Hz). LRMS (ESI/APCI): 257 [M+H]$^+$, 298 [M+H+CH$_3$CN]$^+$.

2-amino-4,4,4-trifluoro-2-methylbutanoic acid

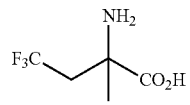

A solution of N-(2-cyano-4,4,4-trifluorobutan-2-yl)-2-methylpropane-2-sulfinamide (4.9 g, 19.1 mmol) in 12 M HCl (5 ml, 60 mmol) and H$_2$O (4 ml) was heated to 90-110° C. for 24 h, then cooled to RT and concentrated in vacuo. The residue was purified by RP-HPLC (H$_2$O/CH$_3$CN) to afford the title compound as a white solid (4.3 g). $^1$H NMR (D$_2$O, 400 MHz) δ 1.57 (s, 3H), 2.73-2.86 (m, 1H), 2.95-3.07 (m, 1H).

2-(Benzyloxycarbonylamino)-4,4,4-trifluoro-2-methylbutanoic acid

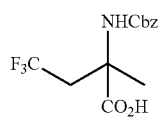

A solution of 2-amino-4,4,4-trifluoro-2-methylbutanoic acid (255 mg, 1.4 mmol) and triethylamine (800 ul, 4.2 mmol) in MeOH (3 ml) was cooled to 0° C. and benzyl chloroformate (509 mg, 2.98 mmol) was added dropwise. The solution was warmed to RT overnight and concentrated in vacuo. The residue was suspended in EtOAc and extracted with sat. NaHCO$_3$, the aqueous layers acidified with conc. HCl, and the resulting milkly suspension extracted with EtOAc. The organic layer was dried over Na$_2$SO$_4$ and concentrated in vacuo to afford the title compound. LRMS (ESI/APCI, negative): 304 [M-H$^+$].

Benzyl 4,4,4-trifluoro-1-hydroxy-2-methylbutan-2-ylcarbamate

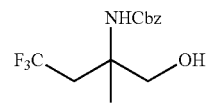

A solution of 2-(benzyloxycarbonylamino)-4,4,4-trifluoro-2-methylbutanoic acid (1.6 g, 5.2 mmol) in THF (17 ml) was cooled to 0° C. and triethylamine (910 ul, 6.5 mmol) was added, then ethyl chloroformate (624 ul, 6.5 mmol) dropwise over 40 min. A solution of sodium borohydride (491 mg, 13 mmol) in H$_2$O (2.6 ml) was added dropwise over 2 h. The reaction was quenched by the addition of 1 M HCl, stirred for 5 min, and then extracted with EtOAc. The organic layer was washed with sat. NaHCO$_3$, sat. NaCl, dried on Na$_2$SO$_4$, and concentrated in vacuo. The residue was purified by flash chromatography (15% to 100% EtOAc in hexanes) to afford the title compound as a clear oil (838 mg). $^1$H NMR (CDCl$_3$, 400 MHz) δ 1.36 (s, 3H), 2.33-2.45 (m, 1H), 2.93-3.03 (m, 1H), 3.62 (br s, 1H), 3.65-3.76 (m, 2H), 5.07-5.10 (m, 3H), 7.28-7.39 (m, 5H). LRMS (ESI/APCI): 292 [M+H]$^+$.

4-methyl-4-(2,2,2-trifluoroethyl)oxazolidin-2-one

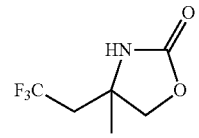

A solution of benzyl 4,4,4-trifluoro-1-hydroxy-2-methylbutan-2-ylcarbamate (830 mg, 2.85 mmol) in THF (55 ml) was cooled to 0° C., and 60% NaH in mineral oil (143 mg, 3.6 mmol) added in one portion. The suspension was stirred for 30 min, then warmed to RT and stirred for 24 h. AcOH (200 ul) added to quench the reaction, and the solution was concentrated in vacuo. The residue was purified by flash chromatography (5% to 20% CH$_3$CN in DCM) to afford the title compound as a white solid (405 mg). $^1$H NMR (CDCl$_3$, 400 MHz) δ 1.47 (s, 3H), 2.43-2.53 (m, 2H), 4.10 (d, J=8.8 Hz, 1H), 4.28 (d, J=8.8 Hz, 1H), 6.84 (s, 1H). $^{19}$F NMR (CDCl$_3$, 376 MHz) δ -61.3 (t, J=10.9 Hz). $^{13}$C NMR (CDCl$_3$, 100 MHz) δ 25.3, 43.0 (q, J=27.2 Hz), 55.0, 75.4, 125 (q, J=277.8 Hz), 158.7. LRMS (ESI/APCI): 184 [M+H]$^+$, 225 [M+H+CH$_3$CN]$^+$.

3-Chloro-4-methyl-4-(2,2,2-trifluoroethyl)oxazolidin-2-one

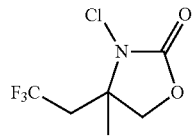

A solution of 4-methyl-4-(2,2,2-trifluoroethyl)oxazolidin-2-one (400 mg, 2.18 mmol) in MeOH (6 ml) was cooled to 0° C. and tert-butylhypochlorite (294 mg, 2.73 mmol) was added. The solution was stirred for 2 h, concentrated in vacuo, and the residue purified by flash chromatography (0% to 10% MeOH in DCM) to afford the title compound as a white solid (350 mg, 74%). $^1$H NMR (CDCl$_3$, 400 MHz) δ 1.54 (s, 3H), 2.48-2.57 (m, 1H), 2.64-2.76 (m, 1H), 4.28 (d, J=8.4 Hz, 1H), 4.45 (d, J=8.8 Hz, 1H). $^{19}$F NMR (CDCl$_3$, 376 MHz) δ −60.93 (t, J=10.5 Hz). $^{13}$C NMR (CDCl$_3$, 100 MHz) δ 20.8, 39.8 (q, J=28 Hz), 62.1, 72.8, 125 (q, J=265 Hz), 155.4. LRMS (ESI/APCI): 259 [M+H+CH$_3$CN]$^+$, 218 [M+H]$^+$.

Example 9

Antimicrobial Activity

Antimicrobial activity of certain compounds of the present disclosure was tested against *Escherichia coli* (ATCC 25922), *Staphylococcus aureus* (ATCC 29213), and *Candida albicans* (ATCC 10231). The microbial cultures were diluted in sterile saline pH 7 to prepare inocula. Test compounds were titrated by stepwise two-fold dilutions in sterile saline pH 7. A total of 1.0×10$^5$ to 1.0×10$^6$ Colony Forming Units (CFU)/mL microbe was added to each tube, mixed by gentle vortexing, and then incubated at room temperature for 1 h. Microbial plating on Petri dishes (Tryptic Soy agar or Saboraud's Dextrose agar) was performed immediately after the designated exposure after neutralization of the test article dilutions in Dey-Engley Broth. Plates were incubated at 37° C., and the numbers of microbes were counted by direct colony count to quantitate the surviving microbes as CFU/mL. Positive growth controls were made with sterile 0.9% saline. Compounds were dissolved phosphate buffered saline (PBS) at pH 7 (using HCl and/or NaOH as needed). All compounds were tested three times.

TABLE 2

| Compound | MBC/MFC (ug/mL) | | | CT$_{50}$ (mM) |
| --- | --- | --- | --- | --- |
| | E. coli | S. aureus | C. albicans | L929 cells |
| 36-01 | 0.5 | 0.5 | >128 | 0.09 |
| 36-02 | 8 | 16 | 512 | 0.04 |
| 36-03 | 2 | 128 | >512 | 0.026 |
| 36-05 | 1 | 0.5 | 64 | 0.1 |
| 36-06 | 1 | 0.5 | 16 | 0.4 |
| 36-07 | 0.5 | 0.5 | 256 | 0.142 |
| 36-08 | 4 | 1 | 128 | 0.232 |

While the foregoing description describes specific embodiments, those with ordinary skill in the art will appreciate that various modifications and alternatives can be developed. Accordingly, the particular embodiments described above are meant to be illustrative only, and not to limit the scope of the invention, which is to be given the full breadth of the appended claims, and any and all equivalents thereof.

We claim:

1. A compound of Formula I

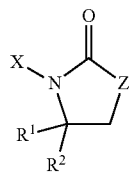

wherein:
X is Cl or Br;
Z is O, NR$^3$ or CR$^3$R$^4$; and
R$^1$, R$^2$, R$^3$ and R$^4$ are each independently H, alkyl or substituted alkyl, with the proviso that at least one of R$^1$ and R$^2$ is a haloalkyl.

2. The compound of claim 1, wherein Z is O.
3. The compound of claim 2, wherein X is Cl.
4. The compound of claim 3, wherein R$^1$ is methyl.
5. The compound of claim 1, wherein Z is NR$^3$.
6. The compound of claim 1, wherein Z is CR$^3$R$^4$.
7. The compound of claim 1, wherein R$^2$ is chloromethyl.
8. A compound selected from the group consisting of:
3-chloro-4-(fluoromethyl)-4-methyloxazolidin-2-one,
3-chloro-4-(chloromethyl)-4-methyloxazolidin-2-one,
3-chloro-4-(bromomethyl)-4-methyloxazolidin-2-one,
3-chloro-4-(2,2,2-trifluoroethyl)-4-methyloxazolidin-2-one,
3-chloro-4,4-bis(chloromethyl)oxazolidin-2-one,
3-bromo-4-(chloromethyl)-4-methyloxazolidin-2-one,
3-chloro-4-(chloromethyl)-1,4-dimethylimidazolidin-2-one,
and 1-chloro-5-(chloromethyl)-5-methylpyrrolidin-2-one.

9. A pharmaceutically acceptable salt of a compound of claim 1.

10. An antimicrobial composition comprising a compound of claim 1, formulated as an aerosol, cream, emulsion, gel, lotion, ointment, paste, powder, solid, solution or suspension.

11. A method for treating a microbial ailment, condition or infection in a subject, comprising administering an effective amount of a compound of claim 1 to the subject.

12. A method for treating a medical device, comprising administering an effective amount of a compound of claim 1 to the device.

* * * * *